(12) United States Patent
Paulus et al.

(10) Patent No.: US 10,226,760 B2
(45) Date of Patent: *Mar. 12, 2019

(54) HYDROGENATION CATALYST AND METHOD FOR PRODUCING SAME

(71) Applicant: Clariant International Ltd., Muttenz (CH)

(72) Inventors: Martin Paulus, Rosenheim (DE); Frank Grossmann, München (DE); Karl-Heinz Stadler, Augsburg (DE)

(73) Assignee: CLARIANT INTERNATIONAL LTD. (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/128,700

(22) PCT Filed: Mar. 19, 2015

(86) PCT No.: PCT/EP2015/055758
§ 371 (c)(1),
(2) Date: Sep. 23, 2016

(87) PCT Pub. No.: WO2015/144548
PCT Pub. Date: Oct. 1, 2015

(65) Prior Publication Data
US 2017/0113209 A1 Apr. 27, 2017

(30) Foreign Application Priority Data
Mar. 26, 2014 (DE) .................. 10 2014 004 413

(51) Int. Cl.
| | | |
|---|---|---|
| *C07C 29/00* | (2006.01) | |
| *B01J 23/00* | (2006.01) | |
| *B01J 33/00* | (2006.01) | |
| *B01J 35/00* | (2006.01) | |
| *B01J 37/00* | (2006.01) | |
| *B01J 27/232* | (2006.01) | |
| *B01J 37/03* | (2006.01) | |
| *B01J 37/04* | (2006.01) | |
| *B01J 37/08* | (2006.01) | |
| *B01J 23/80* | (2006.01) | |
| *B01J 35/10* | (2006.01) | |
| *C07C 29/147* | (2006.01) | |
| *B01J 37/02* | (2006.01) | |

(52) U.S. Cl.
CPC ............ *B01J 27/232* (2013.01); *B01J 23/80* (2013.01); *B01J 35/002* (2013.01); *B01J 35/0046* (2013.01); *B01J 35/0053* (2013.01); *B01J 35/1038* (2013.01); *B01J 35/1042* (2013.01); *B01J 37/0009* (2013.01); *B01J 37/0236* (2013.01); *B01J 37/031* (2013.01); *B01J 37/04* (2013.01); *B01J 37/08* (2013.01); *C07C 29/147* (2013.01); *B01J 2523/00* (2013.01)

(58) Field of Classification Search
CPC . B01J 23/72; B01J 33/00; B01J 35/002; B01J 35/1038; B01J 37/04; B01J 37/08; C07C 29/00
See application file for complete search history.

(56) References Cited

U.S. PATENT DOCUMENTS

| | | | |
|---|---|---|---|
| 4,386,219 A | 5/1983 | Merger et al. | |
| 4,436,833 A * | 3/1984 | Broecker | B01J 23/80 423/420.2 |
| 4,596,782 A | 6/1986 | Courty et al. | |
| 4,666,879 A | 5/1987 | Kelly et al. | |
| 4,762,817 A | 8/1988 | Logsdon et al. | |
| 4,929,771 A | 5/1990 | Clausen et al. | |
| 4,929,777 A | 5/1990 | Irick, Jr. et al. | |
| 5,008,235 A | 4/1991 | Wegman et al. | |
| 5,093,534 A | 3/1992 | Ludwig et al. | |
| 5,122,495 A * | 6/1992 | Taylor | B01J 21/04 502/183 |
| 5,124,295 A | 6/1992 | Nebesh et al. | |
| 5,134,108 A | 7/1992 | Thakur et al. | |
| 5,155,086 A | 10/1992 | Thakur et al. | |
| 5,345,005 A | 9/1994 | Thakur et al. | |
| 5,536,694 A | 7/1996 | Schuetz et al. | |
| 6,337,300 B1 | 1/2002 | Sauer et al. | |
| 6,888,011 B2 | 5/2005 | Borchert et al. | |
| 7,119,237 B2 | 10/2006 | Prinz et al. | |

(Continued)

FOREIGN PATENT DOCUMENTS

| | | |
|---|---|---|
| CN | 102407122 | 4/2012 |
| DE | 20 56 612 | 5/1972 |

(Continued)

OTHER PUBLICATIONS

G.C. Chinchen et al., "The Measurement of Copper Surface Areas by Reactive Frontal Chromatography", Journal of Catalysts, vol. 103, Issue 1, pp. 79-86, Jan. 1987.
PCT International Search Report for PCT/EP2015/055758, dated Jul. 7, 2015.
PCT International Preliminary Report on Patentability for PCT/EP2015/055758, dated Sep. 27, 2016.
Abstract Machine Translation for WO 92/04119, Mar. 19, 1992.
Machine Translation for CN 102407122, Apr. 11, 2012.
United States Patent and Trademark Office Office Action for U.S. Appl. No. 14/432,004 dated Aug. 4, 2016.

(Continued)

*Primary Examiner* — Sikarl A Witherspoon (57) ABSTRACT

A method for producing a shaped Cu—Zn catalyst for hydrogenating organic compounds containing a carbonyl function. The shaped catalyst is suitable for hydrogenating aldehydes, ketones and also carboxylic acids and/or their esters, fatty acids and/or their esters, such as fatty acid methyl esters, to the corresponding alcohols, dicarboxylic anhydrides, such as maleic anhydride (MAn), or esters of diacids to dialcohols, such as butanediol. The present invention further relates to Cu—Zn catalysts obtainable by the production method.

24 Claims, 1 Drawing Sheet

(56) References Cited

U.S. PATENT DOCUMENTS

| | | | |
|---|---|---|---|
| 7,759,530 B2 | 7/2010 | Houssin et al. | |
| 2004/0030163 A1* | 2/2004 | Borchert | B01J 23/72 549/508 |
| 2017/0252727 A1 | 9/2017 | Paulus et al. | |

FOREIGN PATENT DOCUMENTS

| | | |
|---|---|---|
| DE | 30 27 890 | 3/1982 |
| DE | 43 35 360 | 4/1995 |
| DE | 43 45 265 | 9/1995 |
| DE | 10 2005 049135 | 4/2007 |
| DE | 10 2011 086451 | 5/2013 |
| EP | 0 011 150 | 5/1980 |
| EP | 880 996 | 12/1998 |
| EP | 1 338 587 | 8/2003 |
| GB | 1 366 367 | 9/1974 |
| WO | WO 92/04119 | 3/1992 |
| WO | WO 97/34694 | 9/1997 |
| WO | Wo 02/47818 | 6/2002 |
| WO | WO 2006/005505 | 1/2006 |
| WO | WO 2013/072197 | 5/2013 |

OTHER PUBLICATIONS

United States Patent and Trademark Office Office Action for U.S. Appl. No. 14/432,004 dated Dec. 29, 2016.

United States Patent and Trademark Office Notice of Allowance for U.S. Appl. No. 14/432,004 dated Oct. 4, 2017.

* cited by examiner

HYDROGENATION CATALYST AND METHOD FOR PRODUCING SAME

The invention relates to a process for producing a shaped Cu—Zn catalyst body via a carbonate-containing intermediate, and also the catalysts obtainable by means of this process. The catalyst is suitable for the hydrogenation of organic compounds which contain a carbonyl function, in particular for the hydrogenation of aldehydes, ketones and also of carboxylic acids and esters thereof, especially of fatty acids and esters thereof, for example methyl esters of fatty acids, to the corresponding alcohols, dicarboxylic anhydrides, for example maleic anhydride (MAN), or esters of diacids to dialcohols, for example butanediol.

BACKGROUND OF THE INVENTION

In the chemical industry, the hydrogenation of carbonyl compounds, in particular carboxylic acids or carboxylic esters, with the aid of heterogeneous catalysts plays an important role. In principle, both slurry processes and fixed-bed processes are possible for these hydrogenations, with the fixed-bed processes predominating. In the slurry process, the catalysts are used as powders, while shaped catalyst bodies are used in the fixed-bed process.

The hydrogenation of carbonyl compounds is carried out using, in particular, catalysts containing Ni, Cu, Co or noble metals. These can be used as all-active catalysts (e.g. Raney catalysts) or as supported catalysts.

The patent documents DE 43 45 265 and DE 43 35 360 describe shaped Raney catalysts based on Ni, Co, Cu and Fe. These are used for hydrogenating organic compounds. The disadvantage of these catalysts is the addition of metal powders as binders, with the metal powder added being less catalytically active than the Raney metal.

The production of shaped Raney catalysts without addition of binders is described in EP 880 996. These catalysts are used for hydrogenating nitriles. To produce these catalysts, a metal-aluminum alloy present as powder is mixed with a high molecular weight polymer and optionally promoters and subsequently shaped to give shaped bodies. The shaped bodies are calcined at temperatures of up to 850° C., which leads to controlled decomposition of the polymer and formation of a fixed-bed catalyst having sufficient mechanical stability. Activation is effected by leaching out of the aluminum by means of sodium hydroxide solution. However, the leaching out of the aluminum and thus activation of the catalyst occurs only in the outer shell of the shaped body. The core of the catalyst continues to consist of the metal-aluminum alloy used and serves as support for the activated outer layer of the catalyst. As a result, a considerable part of the relatively expensive alloys remains unutilized.

Apart from the Raney catalysts, substantially Cu and Ni catalysts supported on various metal oxides such as $Al_2O_3$ or $SiO_2$ are used for the hydrogenation of carbonyl compounds.

Thus, for example, U.S. Pat. No. 4,666,879 describes an extruded copper chromite-aluminum oxide catalyst produced by mixing of from 40 to 82% by weight of copper chromite and from 18 to 60% by weight of aluminum oxide. The $Al_2O_3$ is typically used in the form of pseudoboehmite or hydroxyboehmite. After calcination, the extruded catalyst is suitable for the liquid-phase and gas-phase hydrogenation and hydrogenolysis of various carbonyl compounds and functional side groups of aromatic compounds. The BET surface area of the extruded catalysts is typically in the range from 125 to 225 $m^2/g$.

U.S. Pat. No. 4,762,817 describes a catalyst for the hydrogenation of aldehydes, which consist essentially of a mixture of copper and zinc oxide. An improvement in the selectivity was able to be achieved by impregnation with alkali metals such as sodium, potassium, lithium or cesium, in combination with a transition metal such as nickel, cobalt or mixtures thereof.

The U.S. Pat. No. 4,929,777 describes catalyst compositions containing oxides of Cu and Ti and the use of such catalyst compositions in the hydrogenation of particular esters to the corresponding alcohols.

The U.S. Pat. No. 5,008,235 describes a process for hydrogenating organic aromatic or nonaromatic acids and esters thereof to give the corresponding alcohols using a coprecipitated catalyst. The catalyst contains copper, aluminum and a further metal such as magnesium, zinc, titanium, zirconium, tin, nickel, cobalt or mixtures thereof and is subjected to reduction before use. The temperature in the reduction is increased stepwise up to a final temperature of from 150° C. to 250° C.

The U.S. Pat. No. 5,093,534 describes a two-stage process for hydrogenating saturated and unsaturated aldehydes to alcohols using Cu- and Ni-containing catalysts. The first stage of the hydrogenation is carried out using a particulate copper catalyst which has been made alkaline. In the second stage of the hydrogenation, a supported nickel-containing catalyst whose support material has acidic sites having a particular acid strength is used.

The U.S. Pat. No. 5,124,295 describes an extruded copper chromite catalyst consisting of a mixture containing from about 20 to 80% by weight of copper chromite and from about 20 to 80% by weight of an extrudable inorganic binder. The catalyst has a specific surface of from about 20 to 225 $m^2/g$ and the total pore volume of the pores in the catalyst is from 0.35 to 1 $cm^3/g$. In one embodiment, this document describes a process for producing a shaped copper chromite catalyst by producing an extrudable mixture, extruding the mixture and calcining the extrudate. The catalysts are employed for the hydrogenation of aldehydes, ketones, carboxylic acids and carboxylic esters.

The U.S. Pat. No. 5,134,108 describes a hydrogenation catalyst comprising oxides of a first metal, copper or zinc, and a second metal, chromium, molybdenum, tungsten or vanadium, and optionally an oxide of a promoter such as manganese, barium, zinc, nickel, cobalt, cadmium or iron. The hydrogenation catalyst is present as a powder having an average particle diameter of from about 6 to 20 μm and a surface area of from about 20 to 70 $m^2/g$. The catalysts are produced by precipitation of the metal salts by means of a base.

U.S. Pat. No. 5,155,086 and U.S. Pat. No. 5,345,005 describe a pulverulent catalyst which consists of a major part of the oxides of copper and zinc and to a smaller part of aluminum oxide, with the atomic ratio of copper to zinc being from 0.2 to 5.5. The catalyst is produced by precipitation, e.g. at a pH of >7, and calcination of the precipitate. The hydrogenation catalysts are used for the hydrogenation of aldehydes, ketones, carboxylic acids and carboxylic esters.

WO 92/04119 describes copper-manganese catalysts for hydrogenating fatty acids and esters thereof. They are produced by admixing an aqueous solution of Cu(II) and Mn(II) salts with sodium hydroxide to form a precipitate of Cu hydroxide and Mn hydroxide. This precipitate is then calcined as powder or in tabletted form. The catalysts obtained have a BET surface area of from about 3 to 45 $m^2/g$.

WO 02/47818 describes catalysts containing Cu oxide for hydrogenating maleic anhydride and derivatives thereof. As pore formers, graphite and ammonium nitrate, in particular, are used here and are mixed into the catalyst powder before tableting. The catalysts for which exclusively graphite has been used as pore former in the production of the catalysts had a pore volume of less than 0.2 cm$^3$/g.

WO 97/34694 describes copper oxide/aluminum oxide hydrogenation catalysts which are produced by precipitation of aqueous solutions of copper nitrate and sodium aluminate by means of sodium carbonate. The material obtained is dried and then calcined at from about 400° C. to 700° C. and subsequently tableted with addition of graphite. The pellets have a pore volume of from 0.2 to 0.6 ml/g and a bimodal pore radius distribution having a first maximum at about 10 nm and a second maximum at from about 50 to a maximum of 200 nm.

In the commercial use of catalysts, an increase in the conversion into the target product is of particularly great interest with a view to achieving a further improvement in the economics.

The conversion of a catalyzed reaction is determined by, inter alia, the activity of a catalyst which in turn is influenced by, inter alia, the magnitude of the "metal surface area" of the catalyst. In general, the term "metal surface area" refers to the accessible surface area of the active component of the catalyst. The catalyst is generally converted into the catalytically active metallic state by reduction of an oxidic precursor of the active component (for example copper in the oxidic form CuO is converted by reduction of Cu(II) to Cu(0)) before actual use. A high Cu metal surface area is associated with a high activity. In general, thermal treatments always lead to more or less pronounced sintering of the metal particles. Sintering reduces the accessible surface area of the active component of the catalyst. Since the reduction of the catalyst usually takes place at elevated temperature, suitable temperature conditions have to be observed in order to keep the sintering effects as small as possible.

In the light of this background, it is an object of the present invention to provide a process for producing tableted catalysts which in the reduced state have a relatively high metal surface area, determined by $N_2O$ pulse chemisorption, compared to catalysts of the prior art.

A further object is to provide tableted catalysts which have a higher activity in hydrogenation reactions than do catalysts of the prior art.

This object is achieved by the process of the invention and the catalysts obtainable thereby.

SUMMARY OF THE INVENTION

The invention relates to a process for producing a shaped tableted catalyst body, which comprises the following steps:
(a) carrying out a thermal treatment of a metal carbonate mixture to give a thermally treated metal carbonate mixture having a carbonate content in the range from 2.7 to 14.0% by weight, preferably in the range from 3.0 to 12.5% by weight, particularly preferably in the range from 3.2 to 12.0% by weight, more preferably in the range from 5.0 to 8.0% by weight, and
(b) tableting the thermally treated metal carbonate mixture obtained in step (a),
wherein:
the metal carbonate mixture is obtainable by
(i) combining a solution A and a solution B to form a precipitate 1, separating off the precipitate and drying the isolated precipitate by heating to a temperature in the range from 75° C. to 130° C.; or
(ii) mixing a precipitate 2, a precipitate 3 and optionally one or more precipitates 4, with the precipitates being dried by heating to a temperature in the range from 75° C. to 130° C. before mixing and/or after mixing, and:
precipitate 2 is a copper carbonate-containing precipitate obtainable by combining a solution C with a solution D,
precipitate 3 is a zinc carbonate-containing precipitate obtainable by combining a solution E with a solution F,
precipitate 4 is a precipitate which contains at least one metal carbonate different from copper carbonate and zinc carbonate and is obtainable by combining at least one solution G with at least one solution H;
and
solution A is obtainable by dissolving a copper compound, a zinc compound and optionally one or more further metal compounds in a solvent, in particular water, optionally with the aid of an acid or base,
solutions B, D, F and H are identical or different and are obtainable by dissolving a carbonate compound in a solvent, in particular water,
solution C is obtainable by dissolving a copper compound in a solvent, in particular water, optionally with the aid of an acid or base,
solution E is obtainable by dissolving a zinc compound in a solvent, in particular water, optionally with the aid of an acid or base, and
solution G is obtainable by dissolving a metal compound which is not a copper or zinc compound in a solvent, in particular water, optionally with the aid of an acid or base.

The carbonate content, in particular of the metal carbonate mixture, is preferably determined in accordance with DIN ISO 10693.

Furthermore, the invention provides Cu—Zn catalysts which can be produced by the processes of the invention.

In addition, the invention provides for the use of Cu—Zn catalysts according to the invention for the hydrogenation of organic compounds, in particular of compounds containing a carbonyl function.

DETAILED DESCRIPTION OF THE INVENTION

The process of the invention for producing a shaped tableted catalyst body comprises the following steps:
(a) carrying out a thermal treatment of a metal carbonate mixture to give a thermally treated metal carbonate mixture having a carbonate content, determined in accordance with DIN ISO 10693, in the range from 2.7 to 14.0% by weight, preferably in the range from 3.0 to 12.5% by weight, particularly preferably in the range from 3.2 to 12.0% by weight, more preferably in the range from 5.0 to 8.0% by weight, and
(b) tableting the thermally treated metal carbonate mixture obtained in step (a).

In one embodiment, the metal carbonate mixture is produced by combining a solution A and a solution B to form a precipitate 1, separating off the precipitate and drying the isolated precipitate by heating to a temperature in the range from 75° C. to 130° C.

Solution A is produced by dissolving a copper compound, a zinc compound and optionally one or more further metal compounds which are not copper or zinc compounds in a suitable solvent in a vessel.

As an alternative, a copper compound, a zinc compound and optionally one or more further metal compounds which are not copper or zinc compounds can be dissolved in a plurality of vessels and the resulting solutions can be combined to form a solution A. Solution B is produced by dissolving a carbonate compound in a suitable solvent.

Precipitate 1 is a copper carbonate-containing, zinc carbonate-containing precipitate which optionally contains a metal carbonate different from copper carbonate and zinc carbonate. The expression copper carbonate-containing precipitate usually refers to a precipitate which contains copper hydroxide carbonate and in which the copper carbonate is present mainly in the form of copper hydroxide carbonate ($x.CuCO_3.Cu(OH)_2$, where x=1 or 2) or generally as mixed carbonate and hydroxide of copper.

In a further embodiment, the metal carbonate mixture is produced by mixing a precipitate 2, a precipitate 3 and optionally one or more precipitates 4, with the precipitates being dried by heating to a temperature in the range from 75° C. to 130° C. before mixing and/or after mixing.

Precipitate 2 is a copper carbonate-containing precipitate and is produced by combining a solution C with a solution D. Precipitate 3 is a zinc carbonate-containing precipitate and is produced by combining a solution E with a solution F. Precipitate 4 is a precipitate containing at least one metal carbonate different from copper carbonate and zinc carbonate and is produced by combining at least one solution G with at least one solution H.

Solution C is produced by dissolving a copper compound in a suitable solvent. Solution E is produced by dissolving a zinc compound in a suitable solvent. Solution G is produced by dissolving a metal compound which is not a copper or zinc compound, in a solvent.

For the purposes of the present invention, the formulation solution encompasses both solutions and also suspensions and slurries, with solutions being preferred.

The solvent is preferably water. An acid or base can be added to the water in order to aid dissolution of the compounds. The water can, for example, have a neutral pH of about 7, an acidic pH of from about 0 to <7, or a basic pH of from >7 to about 14. As a person skilled in the art will know, a pH suitable for dissolving the compounds will be selected as a function of the compound to be dissolved. The water usually has a pH in the range from 4 to 10, preferably from 5 to 9.

As copper compounds and zinc compounds, it is in principle possible to use either copper and zinc in metallic form or preferably all compounds of copper and zinc which are readily soluble in water, acids or alkalis, in particular the salts of the metals mentioned, very particularly preferably their nitrates, carbonates, oxides, hydroxides, hydroxide carbonates, their halides such as chlorides, bromides and/or iodides, and/or their sulfates. When oxides of the metals, e.g. copper oxide and/or zinc oxide, are used for producing the aqueous solutions, then these are preferably partially or completely dissolved by addition of a suitable mineral acid. The copper in copper oxide can be present in one or more different oxidation stats, e.g. copper(I) oxide, copper(II) oxide and mixtures thereof. The mineral acid is preferably selected from among $HNO_3$, HCl, $H_2SO_4$ and mixtures thereof. When the metals themselves, i.e. copper and/or zinc, are used for producing the aqueous solution(s), suspension(s) or slurry/slurries, then these are preferably partially or completely dissolved by addition of suitable acids or alkalis. The dissolution of the metals can, for example, be carried out in inorganic acids or alkalis.

Preferred copper compounds are copper oxide ($Cu_2O$ and/or CuO), copper nitrate, copper chloride, copper carbonate, copper hydroxide carbonate ($x.CuCO_3.Cu(OH)_2$, where x can be 1 or 2), Cu-ammine complexes (e.g. copper tetrammine complexes ($[Cu(NH_3)_4]^{2+}$) or copper hexammine complexes ($[Cu(NH_3)_6]^{2+}$), which can be used, for example, as chloride, hydroxide or sulfate), copper acetate and copper sulfate, in particular copper nitrate. As an alternative, copper metal can also be dissolved in oxidizing acids such as nitric acid ($HNO_3$).

Preferred zinc compounds are zinc nitrate, zinc sulfate, zinc chloride, zinc carbonate, zinc hydroxide, zinc sulfite, zinc acetate and zinc phosphate. As an alternative, zinc metal or ZnO can also be dissolved in acids such as hydrochloric acid (HCl) or nitric acid ($HNO_3$) or in alkalis such as sodium hydroxide (NaOH) or potassium hydroxide (KOH).

Further metal compounds which are not copper or zinc compounds are preferably selected from among compounds of aluminum, silicon, titanium, manganese, nickel, chromium, iron, cobalt, molybdenum, calcium, barium, cerium, zirconium, manganese and mixtures thereof. Particularly preferred metal compounds are the compounds of aluminum, manganese, cerium and zirconium and mixtures thereof. Very particularly preferred metal compounds are the compounds of zirconium and aluminum.

A further metal compound which is not a copper or zinc compound can also comprise metal compounds which contain copper and/or zinc in addition to the metals mentioned. For example, metal compounds which are not copper or zinc compounds can also be mixed metal compounds such as metal complexes which contain copper and/or zinc in addition to one or more of the abovementioned metals. Metal compounds which are not copper or zinc compounds are preferably substantially free of copper compounds and zinc compounds.

As further metal compounds, it is in principle possible to use all compounds of aluminum, silicon, titanium, manganese, nickel, chromium, iron, cobalt, molybdenum, calcium, barium, cerium and/or zirconium which are readily soluble in water, acids or alkalis, in particular the salts of these metals. Instead of or together with the transition metal compounds, it is also possible to use the transition metals in metallic form. Preference is given to using compounds of Mn, Al, Ce and/or Zr. The nitrates thereof, e.g. manganese, aluminum, cerium and/or zirconium nitrate, the halides thereof, e.g. manganese, zinc, cerium and/or zirconium chloride, bromide and/or iodide, the oxides thereof, e.g. manganese, zinc, cerium and/or zirconium oxides, and/or the sulfates thereof, e.g. manganese, zinc, cerium and/or zirconium sulfate, are preferably used.

The carbonate-containing solutions B, D, F and H are produced by dissolving a carbonate compound in a suitable solvent. The solvent is preferably water. An acid or base can be added to the water in order to aid dissolution of the compounds. The water can, for example, have a neutral pH of about 7, an acidic pH of from about 5 to <7, or a basic pH of from >7 to about 13. The water used for dissolving the carbonate preferably has a pH in the range from 5 to 11, more preferably in the range from 6 to 9 and in particular has a neutral pH of about 7. Solutions B, D, F and G can be identical or different from one another. For example, the solutions can have identical or different concentrations of one or more different carbonates and/or have identical or different pH values.

The carbonate compound is preferably selected from the group consisting of alkali metal carbonates such as lithium, sodium, potassium, rubidium or cesium carbonate, alkaline earth metal carbonates such as magnesium, calcium, strontium or barium carbonate, ammonium carbonate and mixtures thereof. It is likewise possible to use the corresponding hydrogencarbonates or any mixtures of carbonates and hydrogencarbonates together with or instead of the carbonates.

Preference is given to using alkali metal carbonates, ammonium carbonates, alkali metal hydrogencarbonates, ammonium hydrogencarbonates or mixtures thereof, particularly preferably alkali metal carbonates and/or hydrogencarbonates.

Preferred alkali metal carbonates are sodium and potassium carbonate, in particular sodium carbonate. Preferred alkali metal hydrogencarbonates are sodium and potassium hydrogencarbonate, in particular sodium hydrogencarbonate. Particular preference is given to using sodium carbonate and/or sodium hydrogencarbonate.

A precipitate is formed by combining a metal-containing solution, e.g. solution A, solution C, solution E or solution G, with a carbonate-containing solution, e.g. solution B, solution D, solution F or solution H. For example, a precipitate 1 is formed by combining a solution A and a solution B. In an analogous manner, a precipitate 2 is formed by combining a solution C and a solution D, a precipitate 3 is formed by combining a solution E and a solution F and a precipitate 4 is formed by combining a solution G and a solution H.

In one embodiment, combining can be effected by introducing the abovementioned solution pairs (for example solution A and solution B; solution C and solution D; solution E and solution F; or solution G and solution H) simultaneously into a joint vessel, for example a precipitation vessel. Here, the two solutions are preferably introduced continuously into the reaction volume of a precipitation mixer. In a further embodiment, combining can also be effected by introducing a solution of the respective solution pair (for example solution A or solution B) into the associated other solution of the respective solution pair (for example solution B or solution A) which has been initially charged, for example in a vessel such as a precipitation vessel. In a preferred embodiment, combining of the solutions is effected by introducing a volume stream of a metal-containing solution (i.e. solution A, C, E or G) into the corresponding carbonate-containing solution which has initially been placed in a precipitation vessel (i.e. solution B, D, F or H).

The metal-containing solutions A, C, E and G are preferably heated to a temperature of 20° C. or more, for example to a temperature in the range from 50° C. to 90° C., in particular to about 80° C., and preferably stirred before the combining step.

Likewise, the carbonate-containing solutions B, D, F and H are preferably heated to a temperature of 20° C. or more, for example to a temperature in the range from 50° C. to 90° C., in particular about 80° C., and stirred before the combining step.

In a preferred embodiment, both the metal-containing solution, for example solution A, and the carbonate-containing solution, for example solution B, are heated to a temperature in the range from 50° C. to 90° C., in particular about 80° C., and stirred.

When solutions of the abovementioned solution pairs (for example solution A and solution B; solution C and solution D; solution E and solution F; or solution G and solution H) are combined, a precipitate is formed in the mixture (hereinafter also referred to as precipitate-containing solution mixture). Combining of the solutions is generally carried out in a stirred vessel. The vessel is preferably stirred by means of an inclined-blade stirrer, propeller stirrer or other commercial stirrers.

The precipitate-containing solution mixture is preferably maintained at a temperature of 20° C. or more and in particular at a temperature in the range from 50° C. to 90° C., preferably about 80° C. In a particularly preferred embodiment of the invention, the precipitate-containing solution mixture is maintained at a temperature in the range from 50° C. to 90° C., preferably at a temperature of about 80° C., for at least 30 minutes, preferably from 1 to 36 hours, in particular about 2 hours, in order to complete precipitate formation if necessary or increase the crystallinity of the precipitate by aging.

Up to completion of precipitate formation, the pH of the precipitate-containing solution mixture is usually kept constant by methods known to those skilled in the art. For example, the rate of introduction of solutions can be selected so that a particular pH is established in the precipitate-containing solution mixture. The pH of the precipitate-containing solution mixture is preferably in the range from 5.0 to 8.5, in particular in the range from 6.0 to 7.5, preferably about 6.8.

The precipitate (i.e., for example, precipitate 1, precipitate 2, precipitate 3, precipitate 4, etc.) is preferably separated off by filtration. As an alternative, the precipitate can also be separated off by decantation or centrifugation.

The precipitate which has been separated off can optionally be subjected to one or more washing steps. Here, the precipitate-containing solution mixture can firstly be separated off from the precipitate by use of a filter press and water can subsequently be passed through the material in the filter press so as to wash the latter. As an alternative, the precipitate which has been separated off can, after the precipitate-containing solution mixture has been separated off by filtration, decantation or centrifugation, be slurried in a vessel and subsequently separated again from the liquid phase by means of a filter press, a centrifuge or a decanter. This operation is generally carried out one or more times until a particular conductivity of the filtrate has been achieved. Here, the conductivity generally correlates with the concentration of sodium ions. The conductivity of the filtrate from the last washing operation is preferably 0.5 mS/cm or less, in particular 0.2 mS/cm or less. The conductivity is determined in accordance with DIN 38404, part 8.

The precipitate which has been separated off and optionally washed is subsequently subjected to drying. Drying is effected by heating the precipitate to a temperature in the range from 75° C. to 130° C., preferably in the range from 90° C. to 120° C. Drying can, for example, be carried out by means of spray drying. For this purpose, a suspension having a solids content of from 10 to 40% by weight is produced from the isolated precipitate, e.g. a filter cake, by means of water. This suspension is then preferably fed into a spray dryer via a nozzle. The temperature in the spray dryer during drying is preferably in the range from 75° C. to 130° C., in particular in the range from 90° C. to 120° C. The output temperature characteristic for drying is preferably in the range from 90° C. to 120° C. and is usually controlled by means of parameters such as amount of suspension sprayed in, the solids content of the suspension (and thus the amount of water which has to be vaporized) or the temperature in the spray dryer. The treatment of the material by means of the spray dryer results, in particular, in a dry powder.

In a preferred embodiment, a metal carbonate mixture (i) is obtained by combining a solution A and a solution B to form a precipitate 1, separating off the precipitate, optionally washing of the precipitate which has been separated off and drying of the isolated precipitate, as described above.

In a further embodiment, a metal carbonate mixture (ii) is obtained by mixing a precipitate 2, a precipitate 3 and optionally one or more precipitates 4. The precipitates 2, 3 and 4 obtained as described above are firstly separated off, optionally washed and subjected to drying by heating to a temperature in the range from 75° C. to 130° C. The separation, optionally washing and drying are carried out as described above. Mixing of a precipitate 2, a precipitate 3 and optionally one or more precipitates 4 is subsequently carried out to give a metal carbonate mixture. Mixing can, for example, be carried out with the aid of a bar or propeller stirrer. As an alternative, the precipitates which have been separated off can be mixed before drying. For this purpose, the precipitates 2, 3 and 4 obtained are firstly, as described above, separated off, optionally washed and mixed with the aid of an Eirich mixer, plowshare mixer or kneader to give a precipitate mixture. The precipitate mixture obtained is subsequently subjected to drying, as described above.

The metal carbonate mixture (i) or (ii) preferably has (after drying by heating to a temperature in the range from 75° C. to 130° C.) a carbonate content of up to 20% by weight, preferably in the range from 10 to 18% by weight. The carbonates present in the metal carbonate mixture are, in the case of copper carbonate, present mainly in the form of copper hydroxide carbonate ($x.CuCO_3.Cu(OH)_2$, where x=1 or 2) or in general as mixed carbonates and hydroxide carbonates of the metal components used.

The metal carbonate mixture (i) or (ii) is, in a step (a), subjected to a thermal treatment until a carbonate content, determined in accordance with DIN ISO 10693, in the range from 2.7 to 14.0% by weight, preferably in the range from 3.0 to 12.5% by weight, more preferably in the range from 3.2 to 12.0% by weight, even more preferably in the range from 5.0 to 8.0% by weight, is attained.

The temperature during the thermal treatment is preferably in the range from 150° C. to 350° C., more preferably in the range from 200° C. to 300° C., particularly preferably in the range from 270° C. to 290° C.

The thermal treatment can be carried out under air or protective gas, for example argon or nitrogen, under oxygen or mixtures thereof. The thermal treatment can be carried out batchwise, e.g. in a tray oven, or continuously, e.g. in a rotary tube oven.

The duration of the thermal treatment is preferably from 5 minutes to 10 hours, more preferably from 1 hour to 6 hours, in particular from 1.5 hours to 5 hours.

In a preferred embodiment, the thermal treatment is carried out for a time of from 1.5 to 5 hours at a temperature in the range from 270° C. to 290° C.

The thermally treated metal carbonate mixture obtained in the above-described step (a) preferably contains 5% by weight or less, more preferably from 0.1 to 4.0% by weight, in particular from 0.5 to 3.0% by weight, of aluminum, based on the total weight of the thermally treated metal carbonate mixture.

The thermally treated metal carbonate mixture obtained in the above-described step (a) is subsequently tableted in a step (b). Tableting is preferably carried out using a tableting press, for example a Korsch tableting press. Tableting makes it possible to obtain pellets having a diameter of from about 1 to 10 mm, preferably from 1.5 to 8 mm and particularly preferably from 3 to 5 mm, and a height of from about 1 to 10 mm, preferably from 1.5 to 8 mm and particularly preferably from 3 to 5 mm. In particular, pellets having a lateral compressive strength, measured in accordance with DIN EN 1094-5, of from 40 to 250 N, preferably from 50 to 160 N, particularly preferably from 60 to 120 N, are produced. The pellets produced by tableting preferably have a diameter in the range from 3 to 5 mm, a height in the range from 3 to 5 mm and a lateral compressive strength in the range from 60 to 120 N.

Tableting is preferably carried out with addition of lubricants such as graphite, oils or stearates, preferably graphite. Here, the thermally treated metal carbonate mixture obtained in step (a) is mixed with lubricants, in particular graphite, optionally compacted and/or granulated and then tableted in step (b). The lubricant is preferably added in an amount in the range from 0.1 to 5% by weight, based on the total weight of the composition to be tableted, before tableting. The lubricant is more preferably added in an amount of from 0.5 to 5% by weight, particularly preferably in an amount in the range from 1 to 4% by weight, based on the total weight of the composition to be tableted.

In a further embodiment, the shaped catalyst body is produced by tableting a mixture of oxidic material and carbonate-containing material. The oxidic material comprises oxides of the metals and/or transition metals used therein, e.g. copper oxide, zinc oxide, aluminum oxide, silicon oxide, titanium oxide, manganese oxide, nickel oxide, chromium oxide, iron oxide, cobalt oxide, molybdenum oxide, calcium oxide, barium oxide, cerium oxide, zirconium oxide and mixtures thereof. Each metal and/or transition metal can be present independently in different stoichiometric compositions with the oxygen. Each metal and/or transition metal can be present independently in one or more different oxidation states. The carbonate-containing material comprises carbonates of the metals and/or transition metals used therein, e.g. copper carbonate, aluminum carbonate, zinc carbonate, silicon carbonate, titanium carbonate, manganese carbonate, nickel carbonate, chromium carbonate, iron carbonate, cobalt carbonate, molybdenum carbonate, calcium carbonate, barium carbonate, cerium carbonate, zirconium carbonate and mixtures thereof. The various components such as oxides and/or carbonates can here originate from different production processes or have been produced by different production routes or, for example, be commercially available raw materials.

In a particularly preferred embodiment, the shaped tableted catalyst body is produced as follows:

a copper compound, a zinc compound and optionally one or more further metal compounds which are not copper compounds or zinc compounds are dissolved in water to give a solution A. A carbonate compound is dissolved in water to give a solution B. Solution A and solution B are combined to form a precipitate 1. Solution A and solution B are preferably combined by introducing a volume stream of solution A into a solution B (which has usually been initially placed in a precipitation vessel). The precipitate 1 formed is separated off, optionally washed and dried by heating to a temperature of from 75° C. to 130° C., as a result of which a metal carbonate mixture (i) is obtained. The metal carbonate mixture (i) obtained is subjected to a thermal treatment (preferably by heating to from 270° C. to 290° C. for from 1.5 to 5 hours). The carbonate content of the thermally treated metal carbonate mixture obtained is determined in accordance with DIN ISO 10693 and is, based on the total weight of the thermally treated metal carbonate mixture, preferably from 2.7 to 14.0% by weight. The thermally treated metal carbonate mixture is subsequently tableted to give a shaped tableted catalyst body.

In a further embodiment, the shaped tableted catalyst body obtained in step (b) is reduced in a step (c).

Reduction is preferably effected by heating the shaped tableted catalyst body in a reducing atmosphere. In particular, the reducing atmosphere is hydrogen. Reduction is carried out, for example, at a temperature in the range from 150° C. to 450° C., in particular in the range from 180° C. to 250° C., preferably in the range from 190° C. to 210° C., particularly preferably at about 200° C. Reduction is carried out, for example depending on the amount of catalyst to be reduced, for a time of from 1 hour (for example for 500 g) to 10 days (for example for 60 metric tons), in particular for a time of from 2 hours to 120 hours, preferably for a time of from 24 to 48 hours. Catalyst amounts on the production scale (for example in the range from 1 to 60 metric tons) are preferably reduced for a time of from 3 to 8 days. In a preferred embodiment, reduction is carried out at a temperature in the range from 190° C. to 210°.

The shaped catalyst bodies are preferably stabilized wet or dry after reduction. In the case of wet stabilization, the shaped bodies are covered with liquid in order to avoid contact with oxygen as far as possible. Suitable liquids include organic liquids and water, preferably organic liquids. Preferred organic liquids are liquids which at 20° C. have a vapor pressure of 0.5 hPa or less. Examples of suitable organic liquids are isodecanol, fatty alcohols such as Nafol® from Sasol, hexadecane, 2-ethylhexanol, propylene glycol and mixtures thereof, in particular isodecanol.

In the case of dry stabilization, a mixture of oxygen or an oxygen-containing gas, preferably air, and an inert gas such as argon or nitrogen is introduced into the reduction reactor. The concentration of oxygen in the mixture is preferably increased from about 0.04% by volume to about 21% by volume. For example, a mixture of air and inert gas in which the ratio of air to inert gas is initially about 0.2% by volume of air to 99.8% by volume of inert gas can be introduced. The ratio of air to inert gas is then gradually increased (e.g. continuously or stepwise) until finally, for example, 100% by volume of air (corresponding to an oxygen concentration of about 21% by volume) is introduced. Without wishing to be tied to a theory, it is assumed that a thin oxide layer having a thickness of, for example, from 0.5 to 50 nm, preferably from 1 to 20 nm, in particular from 1 to 10 nm, is formed on the surface of the catalyst as a result of the introduction of air or oxygen and this thin oxide layer protects the catalyst against further oxidation. In dry stabilization, the reactor temperature is preferably 100° C. or less, even more preferably from 20° C. to 70° C. and particularly preferably from 30° C. to 50° C. After this stabilization, the catalyst is "transportable" and can be transported to the user/plant operator. If step (c) is carried out in-situ in the reactor on the catalyst user's premises, stabilization is dispensed with.

The shaped catalyst bodies according to the invention or the shaped catalyst bodies obtainable by the process of the invention contain, after reduction, Cu(0) (i.e. copper in the oxidation state 0), in particular in a proportion of from 5 to 70% by weight, preferably in a proportion of from 10 to 60% by weight, particularly preferably in a proportion of from 15 to 40% by weight, based on the total weight of the shaped catalyst body.

The shaped tableted catalyst body obtainable by the process of the invention preferably has a pore volume in the range from 0.1 to 0.6 $cm^3/g$, more preferably in the range from 0.13 to 0.40 $cm^3/g$, particularly preferably in the range from 0.15 to 0.25 $cm^3/g$.

The reduced shape catalyst body obtainable by the process of the invention preferably has a pore volume in the range from 0.20 to 0.80 $cm^3/g$, more preferably in the range from 0.22 to 0.70 $cm^3/g$, particularly preferably in the range from 0.25 to 0.35 $cm^3/g$. When the pore volume is to be determined on the reduced shaped catalyst body, the measurement on the shaped catalyst body is preferably carried out with the latter in the dry stabilized form.

In a particularly preferred embodiment, the shaped catalyst body of the invention is present in reduced form and, in dry stabilized form, has a pore volume in the range from 0.20 to 0.80 $cm^3/g$, preferably in the range from 0.22 to 0.70 $cm^3/g$, particularly preferably in the range from 0.25 to 0.35 $cm^3/g$.

The shaped catalyst body obtainable by the process of the invention has, before reduction, a carbonate content in the range from 2.7 to 14.0% by weight, preferably in the range from 3.0 to 12.5% by weight, particularly preferably in the range from 3.2 to 12.0% by weight, more preferably in the range from 5.0 to 8.0% by weight, based on the total weight of the shaped catalyst body.

In a further embodiment, the present invention provides a shaped tableted Cu—Zn catalyst body which, in the reduced and stabilized form, has a pore volume, measured by the Hg intrusion method in accordance with DIN 66133, in the range from 0.20 to 0.80 $cm^3/g$, preferably from 0.22 to 0.70 $cm^3/g$, particularly preferably from 0.25 to 0.35 $cm^3/g$.

In a further embodiment, the present invention provides a shaped tableted Cu—Zn-containing catalyst body which in the reduced form has a Cu metal surface area in the range from 19 $m^2/g$ to 30 $m^2/g$, preferably in the range from 21 $m^2/g$ to 28 $m^2/g$, based on the total weight of the shaped catalyst body. The Cu metal surface area of the catalysts is determined according to the principle of $N_2O$ pulse chemisorption, as is described, for example in G. C. Chinchen, C. M. Hay, H. D. Vandervell, K. C. Waugh, "The measurement of copper surface areas by reactive frontal chromatography", Journal of Catalysts, Volume 103, Issue 1, January 1987, pages 79-86. The Cu metal surface area is determined from the amount of $N_2$ formed, which can be determined by means of a thermal conductivity detector.

In a preferred embodiment, the shaped tableted Cu—Zn-containing catalyst body has a carbonate content in the range from 3.0 to 12.5% by weight and a Cu metal surface area in the reduced form in the range from 19 $m^2/g$ to 30 $m^2/g$. In an even more particularly preferred embodiment, the shaped tableted Cu—Zn-containing catalyst body has a carbonate content in the range from 5.0 to 8.0% by weight and a Cu metal surface area in the reduced form in the range from 21 $m^2/g$ to 28 $m^2/g$.

The shaped catalyst bodies of the invention are suitable for use in numerous reactions. Possible reactions include synthesis gas reactions, methanol syntheses, Fischer-Tropsch syntheses, pyridine syntheses, ester hydrogenolyses, amination reactions, N-alkylations, hydrogenations of nitriles (e.g. acrylonitrile), in particular hydrogenation of nitriles to amines, hydrogenation of esters, in particular fatty acid esters, hydrogenation of diesters (in particular diesters of maleic acid) to diols, hydrogenation of sugars to polyols, alkylation of a phenol by means of an alcohol, amination of an alcohol, dehydrogenation of a primary alcohol to the aldehyde, dehydrogenation of a secondary alcohol to the ketone, dehydrogenation of alkanes (e.g. ethyl benzene or propane) to alkenes (e.g. styrene or propylene), dehydrogenation of cycloalkanes to aromatics, dehydrogenation of diols (e.g. butanediol), hydrogenation of an aldehyde, hydrogenation of an amide, hydrogenation of a fatty acid (e.g. by esterification and subsequent hydrogenolysis), selective hydrogenation of a fat, selective hydrogenation of an oil, hydrogenation of a nitroaromatic hydrocarbon, hydrogenation of a ketone, hydrogenation of furfural and hydrogenation of carbon monoxide or carbon dioxide to form methanol.

In a preferred embodiment, the catalysts produced by the process of the invention are used for hydrogenating carbonyl compounds, in particular for hydrogenating aldehydes, ketones, carboxylic acids and/or esters thereof or dicarboxylic acids and/or diesters thereof, very particularly preferably for hydrogenating fatty acid esters, in particular alkyl esters of fatty acids, preferably methyl esters of fatty acids, or maleic esters.

The catalyst of the invention is particularly suitable for the liquid-phase hydrogenation of carboxylic acids, preferably of fatty acids or fatty acid mixtures having from 5 to 24 carbon atoms, and/or esters thereof, optionally in admixture with alcohols, to form the corresponding fatty alcohols. Here, the fatty acids or fatty acid mixtures can be esterified in-situ with alcohols present in the reaction mixture. Preferred alcohols present in the reaction mixture are fatty alcohols or mixtures of fatty alcohols having from 5 to carbon atoms. Particular preference is given to using the above-described catalyst for hydrogenating methyl esters of fatty acids.

DETERMINATION OF PHYSICAL PARAMETERS

Figure 1:
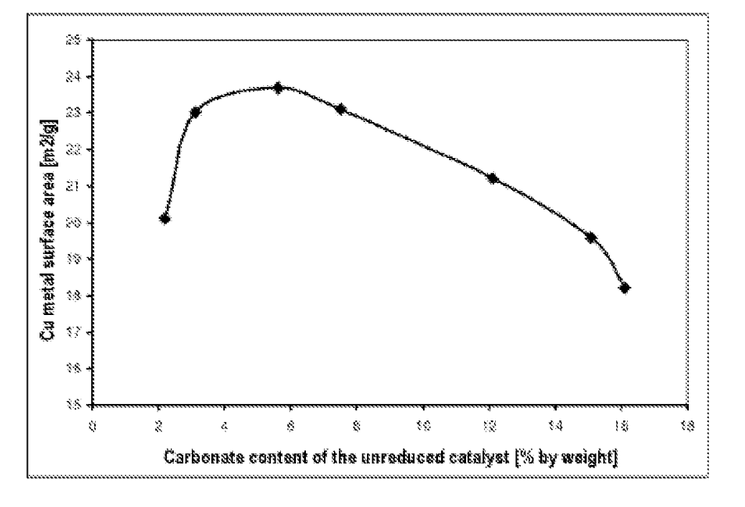
FIG. 1 shows the dependence of the Cu metal surface area (in $m^2/g$ of sample) of the reduced catalysts on the carbonate content (in % by weight of carbonate) of the unreduced catalysts.

The physical parameters described in the present patent application are, unless indicated otherwise, determined as follows:

Conductivity is determined in accordance with DIN 38404, part 8.

Lateral compressive strength is determined in accordance with DIN EN 1094-5.

Residual loss on ignition is determined in accordance with DIN EN 196-2.

Pore volume and pore radius distribution are determined by mercury intrusion in accordance with DIN 66133.

Carbonate content is determined in accordance with DIN ISO 10693.

Cu metal surface area is determined by $N_2O$ pulse chemisorption.

EXAMPLES

The invention is illustrated with the aid of the following, nonlimiting examples. Even though these examples describe specific embodiments of the invention, they serve merely to illustrate the invention and should not be interpreted as restricting the invention in any way. As a person skilled in the art will know, numerous modifications can be made thereto without going outside the scope of the protection of the invention as defined by the accompanying claims.

Reference Example 1 (Production of the Uncalcined Material)

The uncalcined material is produced by precipitation of the metal nitrates by means of sodium carbonate to form their carbonates, and the precipitate is subsequently filtered off, washed and spray-dried.

Solution 1 is produced by dissolving 675 g of ZnO in 1636 g of $HNO_3$ (65% strength) and subsequently adding 1020 g of $Cu(NO_3)_2 \cdot 3H_2O$ and 10 l of deionized water. Solution 2 is produced from 1333 g of $Na_2CO_3$ and 10 l of deionized water. The two solutions are heated to 70° C. and stirred. These are subsequently introduced into a precipitation vessel. The pH in the precipitation vessel is 6.8. The volume flows of solution 1 and 2 are set so that this pH is established. As soon as the two solutions have been used up, the precipitate formed is filtered off and washed with water. The filter cake is then resuspended in about 5 l of water and spray-dried. The resulting dried but still uncalcined pulverulent material is the starting material for the further preparations. The carbonate content of the uncalcined pulverulent material, determined in accordance with DIN ISO 10693, is 16.4% by weight.

Example 1 (Production of Catalyst 1)

For the production of catalyst 1, 100 g of uncalcined material (produced as described in reference example 1) and 2 g of graphite are mixed and tableted to give shaped bodies having a diameter of around 3 mm and a height of about 3 mm. The carbonate content of catalyst 1, determined in accordance with DIN ISO 10693, is 16.1% by weight.

Example 2 (Production of Catalyst 2)

Catalyst 2 is produced by thermally treating uncalcined material (produced as described in reference example 1) for 0.5 hour at 280° C. The carbonate content of this thermally treated powder, determined in accordance with DIN ISO 10693, is 15.4% by weight. 100 g of this thermally treated powder are subsequently mixed with 2 g of graphite and tableted to give shaped bodies having a diameter of about 3 mm and a height of about 3 mm. The carbonate content of catalyst 2, determined in accordance with DIN ISO 10693, is 15.1% by weight.

Example 3 (Production of Catalyst 3)

Catalyst 3 is produced by thermally treating uncalcined material (produced as described in reference example 1) for 1.0 hour at 280° C. The carbonate content of this thermally treated powder, determined in accordance with DIN ISO 10693, is 12.3% by weight. 100 g of this thermally treated powder are subsequently mixed with 2 g of graphite and tableted to give shaped bodies having a diameter of about 3 mm and a height of about 3 mm. The carbonate content of catalyst 3, determined in accordance with DIN ISO 10693, is 12.1% by weight.

Example 4 (Production of Catalyst 4)

Catalyst 4 is produced by thermally treating uncalcined material (produced as described in reference example 1) for 1.5 hours at 280° C. The carbonate content of this thermally treated powder, determined in accordance with DIN ISO 10693, is 7.7% by weight. 100 g of this thermally treated powder are subsequently mixed with 2 g of graphite and tableted to give shaped bodies having a diameter of about 3 mm and a height of about 3 mm. The carbonate content of catalyst 4, determined in accordance with DIN ISO 10693, is 7.5% by weight.

Example 5 (Production of Catalyst 5)

Catalyst 5 is produced by thermally treating uncalcined material (produced as described in reference example 1) for 3 hours at 280° C. The carbonate content of this thermally treated powder, determined in accordance with DIN ISO 10693, is 5.7% by weight. 100 g of this thermally treated powder are subsequently mixed with 2 g of graphite and tableted to give shaped bodies having a diameter of about 3 mm and a height of about 3 mm. The carbonate content of catalyst 5, determined in accordance with DIN ISO 10693, is 5.6% by weight.

Example 6 (Production of Catalyst 6)

Catalyst 6 is produced by thermally treating uncalcined material (produced as described in reference example 1) for 4.5 hours at 280° C. The carbonate content of this thermally treated powder, determined in accordance with DIN ISO 10693, is 3.2% by weight. 100 g of this thermally treated powder are subsequently mixed with 2 g of graphite and tableted to give shaped bodies having a diameter of about 3 mm and a height of about 3 mm. The carbonate content of catalyst 6, determined in accordance with DIN ISO 10693, is 3.1% by weight.

Example 7 (Production of Catalyst 7)

Catalyst 7 is produced by thermally treating uncalcined material (produced as described in reference example 1) for 6 hours at 280° C. The carbonate content of this thermally treated powder, determined in accordance with DIN ISO 10693, is 2.2% by weight. 100 g of this thermally treated powder are subsequently mixed with 2 g of graphite and tableted to give shaped bodies having a diameter of about 3 mm and a height of about 3 mm. The carbonate content of catalyst 7, determined in accordance with DIN ISO 10693, is 2.2% by weight.

Reference Example 2 (Production of Material Calcined at 325° C.)

Calcined material is produced by calcining uncalcined material (produced as described in reference example 1) at 325° C. for 2 hours in a convection oven. The carbonate content of the calcined material, determined in accordance with DIN ISO 10693, is 4.9% by weight.

Example 8 (Production of Catalyst 8)

Catalyst 8 is produced by mixing 15 g of the uncalcined material (produced as described in reference example 1) with 85 g of the powder calcined at 325° C. (produced as described in reference example 2) and 2 g of graphite and tableting the mixture to give shaped bodies having a diameter of about 3 mm and a height of about 3 mm. The carbonate content of catalyst 8, determined in accordance with DIN ISO 10693, is 6.5% by weight.

Comparative Catalyst

A catalyst containing 26% by weight of Cu and 53% by weight of Zn serves as comparative catalyst. The carbonate content, determined in accordance with DIN ISO 10693, is 2.5% by weight. The comparative catalyst is in the form of pellets having a diameter of about 3 mm and a height of about 3 mm and has a pore volume of 210 mm$^3$/g and a Cu metal surface area of 12.8 m$^2$/g.

Example 9 (Activity Measurements)

The activity of the catalysts is examined for the hydrogenation of methyl ester of fatty acid (FAME). An electrically heated fixed-bed reactor having a reactor volume of 25 ml is used for this purpose. Methyl laurate (C12-methyl ester) is used for the test. The reaction product formed is analyzed by gas chromatography to evaluate the ester conversion and the selectivity to the fatty alcohol and the formation of by-products. The conversion is calculated from the molar amount of ester used and the molar amount of ester which remains in the product.

For the analysis by gas chromatography, 6.0000 g of the product formed are mixed with 0.2000 g of 5-nonanol (internal standard). The sample is subsequently analyzed twice using a gas chromatograph.

Equipment Used:
GC: Agilent 7890A with FID
Column: ZB-1, 60 m×0.25 mm from Phenomenex
Software: EZ Chrom Elite Version 3.3.2 SP1
Test conditions in the hydrogenation of methyl laurate:
Reaction temperature: 180° C.
Pressure: 280 bar
GHSV (H$_2$): 20 000 h$^{-1}$
LHSV (ester): 1.4 h$^{-1}$ Table 1 shows the results for the catalysts described as values for the conversions of C12-methyl ester at 180° C. The improved activity of the catalysts according to the invention compared to the comparative catalyst can clearly be seen.

TABLE 1

Conversions of C12-methyl ester at 180° C.

| Catalyst | Conversion of C12-methyl ester at 180° C. [%] |
|---|---|
| Catalyst 1 | 68.0 |
| Catalyst 2 | 74.1 |
| Catalyst 3 | 77.8 |
| Catalyst 4 | 80.0 |
| Catalyst 5 | 80.5 |
| Catalyst 6 | 78.5 |
| Catalyst 7 | 72.0 |
| Catalyst 8 | 79.3 |
| Comparative catalyst | 70.2 |

Determination of the Cu Metal Surface Area

The Cu metal surface area of the catalysts is determined according to the principle of N$_2$O decomposition:

$$2Cu + N_2O \rightarrow Cu_2O + N_2$$

For this purpose, the sample is reduced by means of hydrogen (activation gas 5% of H$_2$ in He) at 240° C. in a TRACE GC ULTRA reduction oven (from Brechbühler) for 16 hours. The sample is subsequently transferred into the TPDRO 1100 series instrument from Thermo Electron, flushed with He and the N$_2$O pulse chemisorptions is started. The Cu metal surface area is calculated from the amount of N$_2$ formed in He, which is determined by means of a thermal conductivity detector.

Table 2 shows the values of the carbonate content of the shaped catalyst before reduction and the Cu metal surface area.

TABLE 2

Carbonate content and Cu metal surface areas

|  | Carbonate content [% by weight] | Cu metal surface area [m²/g of catalyst] |
|---|---|---|
| Catalyst 1 | 16.1 | 18.2 |
| Catalyst 2 | 15.1 | 19.6 |
| Catalyst 3 | 12.1 | 21.2 |
| Catalyst 4 | 7.5 | 23.1 |
| Catalyst 5 | 5.6 | 23.7 |
| Catalyst 6 | 3.1 | 23.0 |
| Catalyst 7 | 2.2 | 20.1 |
| Catalyst 8 | 6.5 | 21.8 |
| Comparative catalyst | 2.5 | 12.8 |

The analytical data show that the carbonate content of the catalysts varies as a function of the duration of the thermal treatment. The carbonate content correlates with the Cu metal surface area of the reduced catalysts. A proportion of carbonate in the range from 3.1 to 12.1% by weight gives a relatively high Cu metal surface area of more than 21 m² per gram of catalyst. The improvement in the activity in the hydrogenation test is coupled thereto.

It can be seen from Table 1 that the catalysts produced according to the invention display a significantly increased conversion of methyl laurate compared to the comparative catalyst.

In summary, it can thus be stated that an improvement in the economics, in particular an increase in the conversion into the target product, is achieved by the catalyst according to the invention.

The invention claimed is:

1. A process for producing a shaped tabletted catalyst body, comprising the steps of:
    (a) carrying out a thermal treatment of a metal carbonate mixture by heating to a temperature in the range from 200° C. to 300° C. for a time of from 1 hour to 6 hours to give a thermally treated metal carbonate mixture having a carbonate content in the range from 2.7 to 14.0% by weight, and
    (b) tableting the thermally treated metal carbonate mixture obtained in step (a),
    wherein:
    the metal carbonate mixture is obtained by
    (i) combining a solution A and a solution B by simultaneous introduction into a joint vessel to form a precipitate 1 at a pH value in the range from 6.0 to 7.5, separating off the precipitate and drying the isolated precipitate by heating to a temperature in the range from 75° C. to 130° C., or
    (ii) mixing a precipitate 2, a precipitate 3 and optionally one or more precipitates 4, with the precipitates being dried by heating to a temperature in the range from 75° C. to 130° C. before mixing, after mixing or both; and:
        precipitate 2 is a copper carbonate-containing precipitate obtained by combining a solution C with a solution D by simultaneous introduction into a joint vessel at a pH value in the range from 6.0 to 7.5,
        precipitate 3 is a zinc carbonate-containing precipitate obtained by combining a solution E with a solution F by simultaneous introduction into a joint vessel at a pH value in the range from 6.0 to 7.5,
        precipitate 4 is a precipitate containing at least one metal carbonate different from copper carbonate and zinc carbonate and is obtained by combining at least one solution G with at least one solution H by simultaneous introduction into a joint vessel at a pH value in the range from 6.0 to 7.5;
    and
        solution A is obtained by dissolving a copper compound, a zinc compound and optionally one or more further metal compounds in a solvent, optionally with the aid of an acid or base,
        solutions B, D, F and H are identical or different and are obtained by dissolving a carbonate compound in a solvent,
        solution C is obtained by dissolving a copper compound in a solvent, optionally with the aid of an acid or base,
        solution E is obtained by dissolving a zinc compound in a solvent, optionally with the aid of an acid or base, and
        solution G is obtained by dissolving a metal compound which is not a copper or zinc compound in a solvent, optionally with the aid of an acid or base.

2. The process as claimed in claim 1, wherein the thermal treatment is carried out at a temperature in the range from 270° C. to 290° C. for a time of from 1.5 to 5 hours.

3. The process as claimed in claim 1, wherein the copper compound is selected from the group consisting of copper, copper oxide ($Cu_2O$ and/or CuO), copper nitrate, copper sulfate, copper carbonate, copper hydroxide carbonate, copper acetate, copper halides, Cu-ammine complexes and mixtures thereof.

4. The process as claimed in claim 1, wherein the zinc compound is selected from the group consisting of zinc nitrate, zinc sulfate, zinc chloride, zinc carbonate, zinc hydroxide, zinc sulfite, zinc acetate, zinc phosphate, zinc metal and ZnO and mixtures thereof.

5. The process as claimed in claim 1, wherein the metal compound, which is not a copper compound or zinc compound, is a compound selected from the group consisting of Al, Ti, Mn, Ni, Cr, Fe, Co, Mo, Ce and Zr and mixtures thereof.

6. The process as claimed in claim 1, wherein the carbonate compound is selected from the group consisting of alkali metal, alkaline earth metal and ammonium carbonates, alkali metal, alkaline earth metal and ammonium hydrogen carbonates and mixtures thereof.

7. The process as claimed in claim 1, wherein the thermally treated metal carbonate mixture contains 5% by weight or less, based on the total weight of the thermally treated metal carbonate mixture.

8. The process as claimed in claim 1, wherein a lubricant is added in an amount of from 0.1 to 5% by weight, based on the total weight of the composition to be tabletted, to the thermally treated powder obtained from step (a) before tableting.

9. The process as claimed in claim 8, wherein the lubricant is added in an amount of from 0.5 to 5% by weight, based on the total weight of the composition to be tabletted.

10. The process as claimed in claim 8, wherein the lubricant is graphite.

11. The process as claimed in claim 1, further comprising the step of:
    (c) reducing the shaped tabletted catalyst body obtained from step (b) to give a reduced shaped catalyst body.

12. The process as claimed in claim 11, wherein reduction is effected by hydrogen.

13. The process as claimed in claim 11, wherein reduction is carried out at a temperature in the range from 150° C. to 400° C.

14. The process as claimed in claim 11, wherein reduction is carried out over a time of from 1 hour to 10 days.

15. The process as claimed in claim 11, wherein
   (a) the reduced shaped catalyst body is covered with a liquid with exclusion of air after reduction, or
   (b) a mixture of an oxygen-containing gas and an inert gas is supplied to the reduced shaped catalyst body with the concentration of oxygen in the mixture during introduction being from 0.001% by volume to 50% by volume.

16. A shaped tableted catalyst body obtained by a process as claimed in claim 1.

17. The shaped tableted catalyst body as claimed in claim 16, having a carbonate content in the range from 2.7 to 14.0% by weight.

18. A reduced shaped tableted catalyst body obtained by a process as claimed in claim 11, wherein the shaped tableted catalyst body obtained from step (b) has, before reduction, a carbonate content in the range from 2.7 to 14.0% by weight.

19. The reduced shaped tableted catalyst body as claimed in claim 18, whose Cu metal surface area is 19 $m^2/g$ or more, based on the total mass of the catalyst.

20. The shaped tableted catalyst body as claimed in claim 18, containing Cu(0) in a proportion in the range from 5 to 70% by weight, based on the shaped tableted catalyst body.

21. A method for hydrogenating an organic compound comprising the step of exposing the organic compound to a shaped tableted catalyst body as claimed in claim 16, during manufacture of the organic compound.

22. The method as claimed in claim 21 where the organic compound has at least one carbonyl group.

23. The method as claimed in claim 21, wherein the organic compound is selected from the group consisting of aldehydes, ketones and monocarboxylic, dicarboxylic and polycarboxylic acids and/or esters thereof.

24. A method for catalyzing a reaction comprising the step of exposing the reaction to a shaped tableted catalyst body as claimed in claim 16, wherein the reaction is selected from the group consisting of synthesis gas reactions, methanol syntheses, Fischer-Tropsch syntheses, pyridine syntheses, ester hydrogenolyses, amination reactions, N-alkylations, hydrogenations of nitriles, hydrogenation of esters, hydrogenation of diesters to diols, hydrogenation of sugars to polyols, alkylation of a phenol by means of an alcohol, amination of an alcohol, dehydrogenation of a primary alcohol to the aldehyde, dehydrogenation of a secondary alcohol to a ketone, dehydrogenation of alkanes to alkenes, dehydrogenation of cycloalkanes to aromatics, dehydrogenation of diols, hydrogenation of an aldehyde, hydrogenation of an amide, hydrogenation of a fatty acid, selective hydrogenation of a fat, selective hydrogenation of an oil, hydrogenation of a nitroaromatic hydrocarbon, hydrogenation of a ketone, hydrogenation of furfural and hydrogenation of carbon monoxide or carbon dioxide to form methanol.

* * * * *